United States Patent [19]

Polanin

[11] 4,178,688
[45] Dec. 18, 1979

[54] REMOVING POST FROM HUMAN BONY STRUCTURE

[76] Inventor: Walter R. Polanin, 17802 Dogwood La., Hazel Crest, Ill. 60429

[21] Appl. No.: 781,019

[22] Filed: Mar. 24, 1977

[51] Int. Cl.² .................................................. A61C 3/02
[52] U.S. Cl. ..................................... 433/220; 433/75
[58] Field of Search ................... 32/43, 44, 45, 46, 12, 32/13; 128/92 E, 305

[56] References Cited

U.S. PATENT DOCUMENTS

| | | | |
|---|---|---|---|
| 1,102,850 | 7/1914 | Arden | 32/44 |
| 1,123,730 | 1/1915 | Greenfield | 32/48 |

*Primary Examiner*—Robert Peshock

[57] ABSTRACT

A post broken off from a cap previously retained in human bony structure, such as a human tooth, is removed from a hole in the tooth within which the post has been retained, as by cement. The removal is effected by a hollow rotary drill having tooth cutters surrounding the post, said drill while rotating being urged into the hole until the cutters have released the post from the surrounding cement. Preferably an adjustable stop is provided within the drill to abut the outer end of the post when the cutters have reached the inner end thereof, to prevent damage to the root structure beyond the inner end of the post. The inner diameter of the drill closely fits the outer diameter of the post so that it acts as a guide for the cutters as they are urged into the hole within which the post is retained.

6 Claims, 7 Drawing Figures

REMOVING POST FROM HUMAN BONY STRUCTURE

This invention relates to the art of dentistry and more particularly to the removal from a hole in human bony structure, such as a human tooth, of a post broken off from a cap previously applied to the tooth, as by cement.

A primary object of the invention is to remove the cement from around the post by a hollow rotary drill having tooth cutters surrounding the post, the cutters being urged into the hole within which the post is contained as the drill rotates.

Another object of the invention is to guide the drill by means of the post itself. This is accomplished by having the inner diameter of the drill closely fit the outer diameter of the post. Still another object of the invention is to provide a stop, preferably adjustable, within the drill for abutment with the outer end of the post when the cutters reach the inner end thereof. The adjustable stop will provide any number of settings and therefore afford economic benefits over a non adjustable hollow rotary drill.

The foregoing and other objects and advantages of the invention will become apparent from the following specification and the accompanying drawings, wherein.

Figure 1:
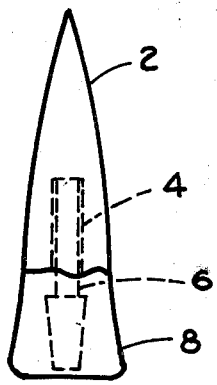
FIG. 1 is an enlarged elevational view of a human tooth with a cap and its post applied thereto.

Describing the invention in detail and referring first to FIG. 1, a capped tooth 2 contains a hole 4 into which a post 6 integral with or fixed to the cap 8 is snugly fitted and surrounded by cement 10 in the usual manner.

Figure 2:
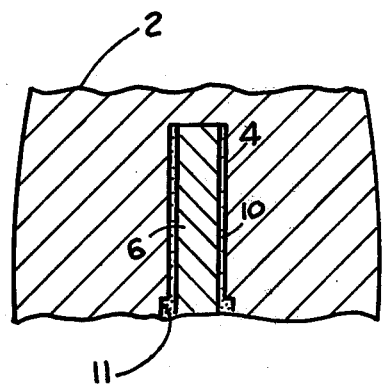
FIG. 2 is a further enlarged fragmentary central vertical sectional view of the structure shown in FIG. 1 with the cap broken off.
Figure 5:
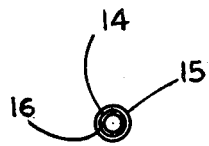
FIG. 5 is a top plan view thereof.
Figure 4:
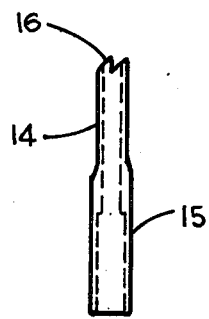
FIG. 4 is an elevational view of the novel drill.
Figure 7:
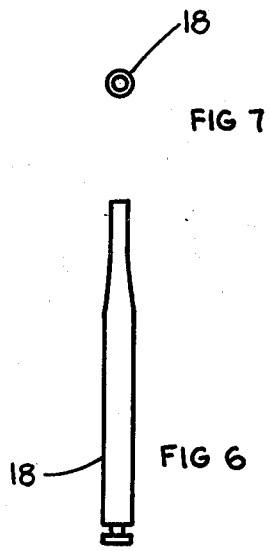
FIG.7 is a top plan view thereof.
Figure 6:
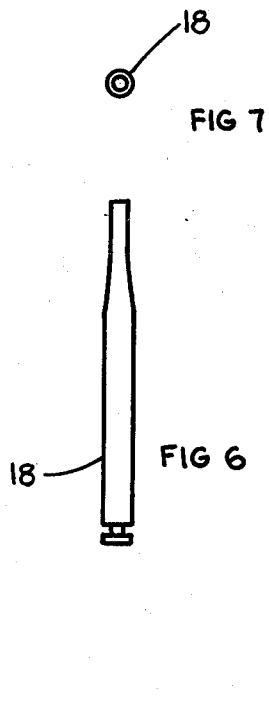
FIG. 6 is an elevational view of the novel stop rod.

In the event that the post is accidentally broken off, as shown in FIG. 2 as by an impact against cap, there has been no successful technique for removing the post until the invention hereinafter described.

A hollow cylindrical drill 14 is provided having cutter teeth 16 on one end thereof. The inner diameter of the drill is approximately 0.005 of an inch greater than the outer diameter of the post 6 so that the drill snugly surrounds the post as the cutters 16 are urged into the hole 4.

Figure 3:
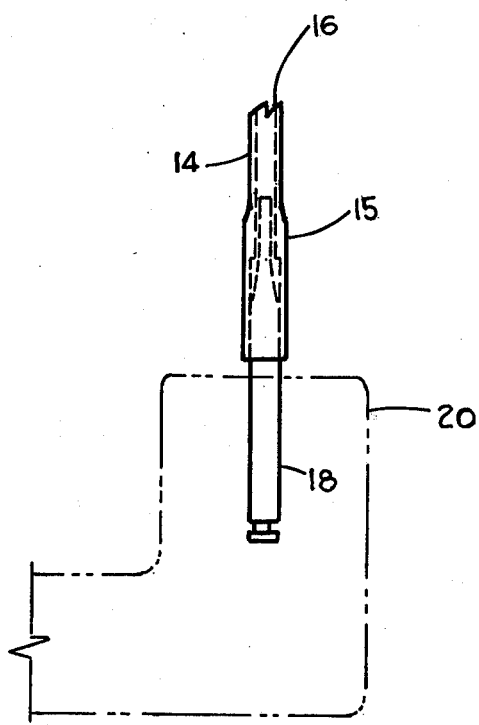
FIG 3 is an elevational view of the novel drill and stop rod assembly utilized in the practice of the invention.

Preferably, a cylindrical stop rod 18 is snugly and slideably fitted within the complementary inner diameter of the drill 14 so that the rod abuts the outer end of the post 6 when the cutters 16 reach the inner end thereof. The proper distance between the rod 18 and the cutters 16, as shown in FIG. 3, may be determined by measurement of an X-ray of the tooth so that the rod may be secured to the drill at said proper distance by any suitable means such as an adhesive or set screw (not shown) in a larger diameter segment 15 of the drill 14.

After the stop rod 18 has been fixed or locked within the drill cylinder 14 in proper spacing from the cutters 16, preferably enough of the cement is chipped away to form a counter bore 11 and exposing enough of the post 6 at its outer end to fit into the drill cylinder 14 so that the post 6 may act as a guide for the drill cylinder 14 as it is rotated as hereinafter described, and urged into the hole 4 around the post 6. When the stop rod 18 abuts the outer end of the post, the dentist knows that the cutters 16 have reached the inner end of the post whereupon the drill is removed and the post is withdrawn from the hole. If a slight amount of cement on the inner end of the post inhibits its withdrawal the post may be rocked slightly to break the cement bond at the inner end of the post whereupon it may easily be withdrawn.

After the drill 14 and the stop rod 18 have been locked together in the proper position (FIG. 3) they rotate as a unit so that the rod 18 affords a convenient connection to a conventional dental tool holder 20 having means (not shown) to rotate the drill 14.

Initial rotation of the drill and rod 18 by hand is preferable until the cutters have entered that portion of the hole 4 inwardly of the counter bore 11. Thereafter using the post as a guide, the dentist using correct variable drill rotating speeds afforded by the tool holder 20 cuts away the cement and minimum tooth structure until the post 6 is released from the hole 4 as heretofore described. During this power drilling operation, it may be necessary, from time to time, to remove the drill and flush out the hole 4 as well as the cutters 16, as by a stream of water or compressed air, and then resume the power drilling until the operation has been completed.

After the post 6 has been removed, a new cap may be applied, as shown in FIG. 1, to afford a restorative technique far superior to those in use prior to this invention.

It may be noted that the cutters 16 are preferably entirely in the plane of the cylindrical wall of drill 14 to avoid unnecessary cutting of tooth structure in removing the post 6. However, where removal of tooth structure is not too critical the cutters 16 may extend out of the cylindrical wall slightly to afford design of cutters most suitable. The outer diameter of the drill 14 may be, for example, of the order of about 0.098 of an inch, but the structure is shown at a larger scale for the sake of clarity. The cylindrical wall of drill cylinder 14 is preferably of the order of about 0.008 of an inch in thickness and the larger diameter segment 15 is preferably of the order of 0.125 of an inch in outer diameter.

While the invention has been shown in but one form, it will be obvious to those skilled in the art that it is not so limited but is susceptible of various changes and modifications, such as having the cutter diameters 14 and 15 the same and a uniform inner diameter throughout the length of the cylindrical cutter, without departing from the spirit of the invention or the scope of the claims.

What is claimed is:

1. In a method of removing a post secured within a hole of a human tooth, the steps of measuring the length of said post in an x-ray picture thereof, then positioning a rod within a cylindrical drill having tooth cutters at one end and locking said rod within said drill with the inner end of said rod at a distance from said cutters approximately equal to the length of said segment and then rotating said drill with said cutters positioned around said post while forcing said drill toward the inner end of said hole until said rod abuts said post.

2. In a method of removing a post segment secured within a hole of a human tooth, the steps of positioning a hollow drill having tooth cutters at one end surrounding said post and having an internal diameter greater than said post segment and then rotating said drill with said cutters positioned around the exposed end of said segment while forcing said drill cutters toward the inner end of said post segment until said post segment is free from retention in said hole from end to end thereof.

3. A method according to claim 2 wherein the post segment engages a stop abutment within the drill to limit movement of the cutters into the hole.

4. In a method of removing a post secured within a hole of a human tooth, the steps of surrounding said post with an annulus of interconnected tooth cutters and then rotating the annulus while forcing the cutters into said hole around said post toward the inner end thereof until the post is freed from said tooth to the inner end of the hole and then pulling the post from said hole.

5. In a method of removing a post segment from a hole in a human tooth, the steps of inserting a rod into one end of a cylinder within which the segment is snugly and slideably receivable, then advancing said rod within said cylinder toward the opposite end thereof which comprises cutters disposed in the cylinder wall, to a position at which the distance between the inner end of the rod and said opposite end of said cylinder is approximately equal to the length of the segment and fixing the rod in that position against rotation relative to the cylinder, connecting the other end of said rod to a drill holder having means to rotate the rod, and then actuating said means to rotate said rod while said cutters surround said segment and while urging the cylinder toward the inner end of said hole until the segment abuts the rod.

6. A method according to the claim 5 wherein the cutters are entirely within the plane of the cylinder wall.

* * * * *